(12) United States Patent
Hajdu

(10) Patent No.: US 8,756,875 B2
(45) Date of Patent: Jun. 24, 2014

(54) REGULAR QUADRILATERAL PYRAMID BUILDING AND PROCEDURE FOR OPERATION THEREOF

(76) Inventor: Imre Hajdu, Bekescsaba (HU)

( * ) Notice: Subject to any disclaimer, the term of this patent is extended or adjusted under 35 U.S.C. 154(b) by 0 days.

(21) Appl. No.: 13/697,144

(22) PCT Filed: Mar. 1, 2011

(86) PCT No.: PCT/HU2011/000018
§ 371 (c)(1),
(2), (4) Date: Nov. 9, 2012

(87) PCT Pub. No.: WO2012/104664
PCT Pub. Date: Aug. 9, 2012

(65) Prior Publication Data
US 2013/0055655 A1    Mar. 7, 2013

(30) Foreign Application Priority Data
Feb. 2, 2011   (HU) ..................................... 1100056

(51) Int. Cl.
*E04B 1/32*   (2006.01)
(52) U.S. Cl.
USPC .............................................. 52/82; 52/292

(58) Field of Classification Search
USPC ....................... 52/82, 292, DIG. 10
See application file for complete search history.

(56) References Cited

U.S. PATENT DOCUMENTS

2009/0277127 A1* 11/2009 Vasquez et al. ............. 52/741.11
2011/0133940 A1*  6/2011 Margalit ....................... 340/584

FOREIGN PATENT DOCUMENTS

EP          2090720      * 8/2009   ............... E04H 1/02

* cited by examiner

*Primary Examiner* — Brian Glessner
*Assistant Examiner* — Adam Barlow
(74) *Attorney, Agent, or Firm* — Abe Hershkovitz; Hershkovitz & Associates, PLLC

(57) ABSTRACT

A regular quadrilateral pyramid-shaped building has isosceles triangle-shaped supporting side walls and a square-shaped base, with a free pyramid-shaped internal space and with a podium in the pyramid-shaped space. The side walls and the base of the pyramid building are made of several layers; the external layer of the side walls and the external layer of the base facing the ground are made of walling units; the internal layer of the side walls and the internal layer of the base are made of electrically controllable covering units.

8 Claims, 8 Drawing Sheets

REGULAR QUADRILATERAL PYRAMID BUILDING AND PROCEDURE FOR OPERATION THEREOF

CROSS-REFERENCE TO RELATED APPLICATIONS

This application is a submission under 35 U.S.C. §371 entering the national stage in the United States for International Application No. PCT/HU2011/000018 filed on Mar. 1, 2011, and claiming priority from Hungarian Patent Application No. P01100056 filed on Feb. 2, 2011.

BACKGROUND OF THE INVENTION

1. Field of the Invention

The subject of the invention is a regular quadrilateral pyramid-shaped building which has isosceles triangle-shaped sidewalls on a square-shaped base, free pyramid-shaped internal space, and a podium in the pyramid-shaped space. The invention also includes the procedure for the operation of the pyramid building.

2. Description of Related Art

Mankind has been interested in the collection and use of energies detected in nature for a long time, especially in their use for medical purposes.

Recently, we may find medical devices that facilitate re-energizing and may be used successfully for a wide range of purposes. Others, such as Biotron lamps, use polarized light successfully to cure wounds, such as ulcers. Recently, treatment has also been extended to the use of multi-colour light. The exact effect mechanism of such treatments is yet to be known thoroughly, but their advantageous medical effects justify their uses. Similarly, people living in strong electromagnetic fields and close to high-voltage pylons suffer from headache and bad general condition as a result of such fields, while on-spot measurements do not justify their conditions.

Egyptian pyramids and the mysterious phenomena experienced in their burial vaults have been exciting mankind since the ancient times. Recent researchers have revealed various issues, and have rebutted several superstitions, but there are many questions yet to be answered concerning the energy fields—their nature, effect mechanism—inside pyramids that affect both objects and living creatures. Such fields are usually referred to in patent descriptions as pyramid energy, and the processes induced by them in objects and living creatures are called energising. This may include the energetic charging or, adversely, the reduction of the extremely high energy levels of overcharged objects, such as stressed living creatures. This way pyramid energy may help in restoring the internal bio-vibration of human beings and creating a healthy human aura. The emergence of pyramid energy is associated by most people with the strict compliance of the size of pyramids, the specific size of the base and of the edges, and with the proportions thereof. In our experiences, the directions—relating to the four cardinal points—of the four sides of the pyramid are also important for creating pyramid energy and for its energy level. The patent research conducted on this subject shows that the issue—especially its relaxing, health reservation and caring, curing roles—has been widely examined during the previous century and is still a major subject of research. At wellness service providers, such as non-medical practitioners, these solutions may help cure patients with depression and psychosomatic diseases.

During the last century, researchers in Hungary have also been—and are still—working on solutions on this matter and applying for patent and utility model protection. Some of the patent and utility model descriptions submitted for registration on this subject in Hungary may also be used for presenting the directions of research. An example is the patent description of the "Pyramid shaped energy collector sunhat" No. HU P9103126. The sides of the sunhat represent a pyramid-shaped geometric form consisting of isosceles triangle side panels that close identical angles with each other at the top of the pyramid. The hat has a relaxing, curing, and energizing effect on the person wearing it. It is advantageous for energizing purposes, if one of the base edges of the hat is pointed in the North-South direction while wearing the hat. However, it is hard to keep this rule while moving around. According to the patent description, the benefit of alignment with the four cardinal points is an important empirical fact for hat-sized pyramid buildings.

The "Device for accelerating growth" patent description No. HU P9203085—originally of Austrian priority—describes a device that may be used for promoting and accelerating the growth of human beings and animals, and for restoring their health conditions after suffering injuries. An interesting feature is that the device—in addition to regular quadrilateral pyramids—uses other geometric forms, such as pyramids with hexagonal bases. This seems to contradict the widely held position that a field force of appropriate strength emerges only in regular quadrilateral pyramids.

The utility model No. U 2218 describes a "Device for utilizing pyramid energy". The device is a spiral-shaped medical device—such as an arch-support—consisting of numerous pyramid-shaped—that is quadrilateral pyramid-shaped—parts. On the basis of the Fibonacci principle, the small-sized pyramids are organized in spiral lines around each other running from different starting points.

The utility model No. U 2222 describes a "Disc containing pyramid shaped parts" using similar small-sized pyramids, but organized in ordinary lines on a disc, unlike the spiral implementation mentioned in the previous description.

There are various Hungarian descriptions of pyramid-shaped items and items containing pyramid-shaped parts, that use "pyramid energy" for various purposes, but these are far from the solution according to our invention.

Internationally, there are various patents using pyramid-shaped forms for different purposes or that exploit pyramid energy. The "Pyramidenenergieanlage" invention No. US 2010207399 and No. EP 0259769 is used to exploit energy.

The author of the German description No. DE 197 17 053 uses, for medication purposes, pyramids made of special aluminium alloy, that are of empirically specified size and are placed on human skin above certain organs.

Some of the examined inventions are close to the solution according to our invention. The European description "Pyramidenförminges Gebaude" No. EP 2 090 720 describes a pyramid-shaped building for treating stressed or agitated persons. The side walls of the building made of wood or cane batches have windows, though many believe that any windows on the walls of pyramid buildings actually reduce the efficiency of pyramid energy and may even prevent its emergence.

The utility model "Pyramide mit energieverstaerkender Fokussiereinrichtung" No. DE 20 2006 004 778 and the pyramid building described in the Japanese "Meditation Room" invention No. JP 8074133 may be the closest to the solution according to our invention.

The essence of the German utility model is that the focusing rods—that are producing pyramid energy and are installed in the building—partially support the platform exposed the most to the effects of the energy, and also focus pyramid energy on the object to be energized. The utility model also describes the "Bovis factor" (BE) as the measurement unit of the undefined strength of pyramid energy. According to this factor, the neutral level—for example—of buildings, water or foodstuff is 6.500 BE. As an interesting fact, it is noted that the empirical Bovis factor level—measured by radiologists—of distilled water is 3.000 BE, of the Himalayan salt is 18.000 BE, and it was measured to be 170.000 BE in the burial vault of the Cheops Pyramid. The measurement method of the BE factor is yet to be acknowledged scientifically.

The above-mentioned Japanese patent description describes the structure of an entire meditation house, where the top level of the building is designed for meditation, relaxation and medical treatment purposes using pyramid energy. The description does not mention any separate podium in this space. The top level of the building may be approached on a spiral staircase from the lower level with windows and lighting. The sides and floor of the top-level pyramid-shaped part of the building is made of one layered transparent or translucent material, with a cap on top, and there is a roof—made of copper or steel—above the entrance. The entire building, especially its top level, is in close relation with its environment, with the outside space full of cosmic and other radiations. Though the building with its mysterious lights in the evening may be suitable for mediation, it is clearly dominated by force fields that are completely different from those dominating the internal burial vaults of pyramids surrounded by thick walls, or the hermetically sealed internal space of the pyramid building with multi-layered thick walls according to our invention, as it will be described below.

BRIEF SUMMARY OF THE INVENTION

The purpose of our invention is to create a building, in which we could provide advantageous conditions for the emergence of the so-called pyramid energy effects that are suitable for energizing living beings and objects. It is suitable—for example—to restore the bio-vibration of the human body to ensure that the cells enjoy the most suitable vibration energy in the appropriate frequency range, that they are well balanced, and are elevated to a higher vibration level, thus strengthening the electro-magnetic energy shell and aura of the human body.

The invention is based on the recognition that if, on the one hand, the external cosmic and other electro-magnetic fields as well as the earth radiation effects coming from below are reduced or eliminated in the inside of the building and, on the other hand, an energizing field of the desired frequency, amplitude, and frequency spectrum is created in the resulting hermetically sealed space, which is regulated in time and space with our procedure, we can achieve our objective.

We have also recognized that it is possible to replace the several meter thick walls of pyramids with much thinner walls, if the external layer of the walls and the lower layer of the base—which is facing the earth—are made of walling units dominated by positive ions, while the internal layers are made of covering units dominated by negative ions. Between the two layers, there is also an electrically sealing middle layer, which maintains the dominance of the external positive ions and of the internal negative ions, which middle layer also ensures the fixing or pasting of the external and internal layers, walling units, and covering units. In the inside of the pyramid building surrounded by covering units, the most advantageous conditions are ensured that may be necessary for the emergence of pyramid energy by placing controllable and vibrating piezoelectric units and trans-illuminating blue LED light sources on the side of the covering units—made of translucent material—facing the walling units, which may be controlled from the central control device.

Our invention is: a regular quadrilateral pyramid-shaped building, which has isosceles triangle-shaped supporting side walls, a square-shaped base, and is fitted with a podium inside the pyramid-shaped space.

BRIEF DESCRIPTION OF THE DRAWINGS

The pyramid building and the procedure for its operation according to the invention is presented in detail on drawings, where.

DETAILED DESCRIPTION OF THE INVENTION

Figure 1:
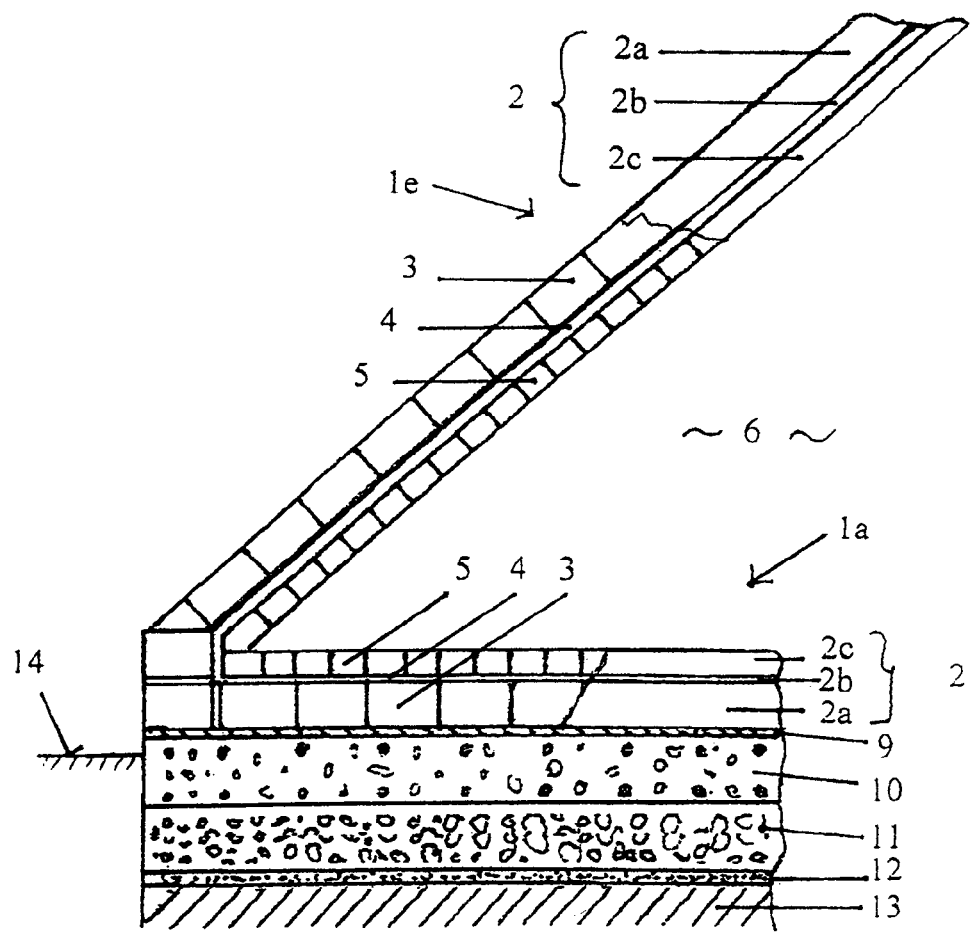
FIG. 1 shows the structural parts in a corner segment of the pyramid building, partially as a section.

As shown clearly on FIG. 1, the side walls of the pyramid-shaped building are made of several layers. It is also clear from the drawing, that in this embodiment, not only the side walls are made of three layers—an external layer 2a, a middle layer 2b, and an internal layer 2c—, but the base 1a as well. According to the invention, it is also possible to use more than three layers to reduce the effects of external fields and/or to promote the emergence of pyramid energy in the internal space 6. It is also apparent on the section drawing of the corner that the external layer 2a is made of walling units 3, the middle layer 2b is made of water and electric insulating mortar 4, and the internal layer 2c is made of covering units 5. The support and stability of the trussing of the entire building is ensured by the walling units 3, which—in an advantageous embodiment—are made of limestone shapes, limestone bricks. The covering units 5 surrounding the pyramid-shaped internal space 6 and covering the floor are fixed to the walling units 3 with water and electric insulating mortar 4. Thus, a pyramid-shaped internal space 6—which is closed from every direction, including from below—is created inside the pyramid building. In an advantageous embodiment, the covering units 5 are made of amorphous native salt shapes, preferably panels. The best materials for this purpose are Tibetan salts and Nepalese salts. The entire pyramid building is built on a foundation prepared in an excavated trench in the ground 13. The foundation is also made of several layers, the lowest layer is sand 12, followed by the crushed rock-bed 11, steel-concrete 10, and the base insulator plate 9 is the top layer connecting to the top layer of the external layer 2a of the pyramid building. The necessary foundation is always to be in compliance with the prevailing construction regulations.

Figure 2:
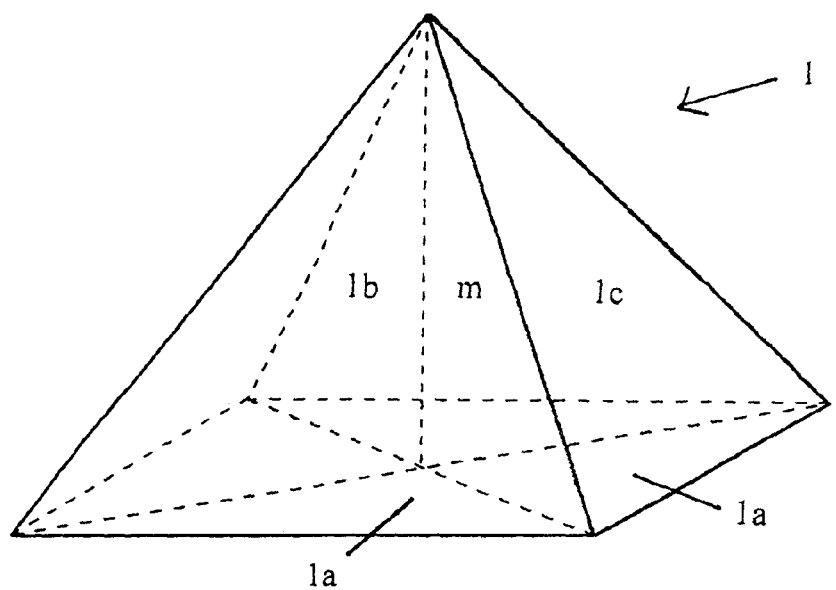
FIG. 2 shows the perspective view of the outside of the pyramid building.
Figure 3:
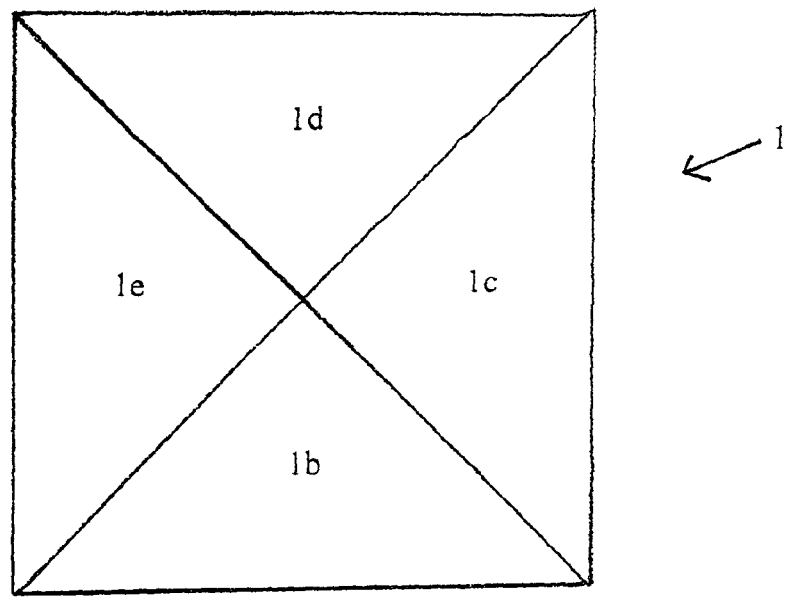
FIG. 3 shows the bird's-eye view of the pyramid building.

FIGS. 2 and 3 show perspective and bird's-eye view of the outside of the pyramid building 1 with side walls 1b, 1c, 1d and 1d.

Figure 4:
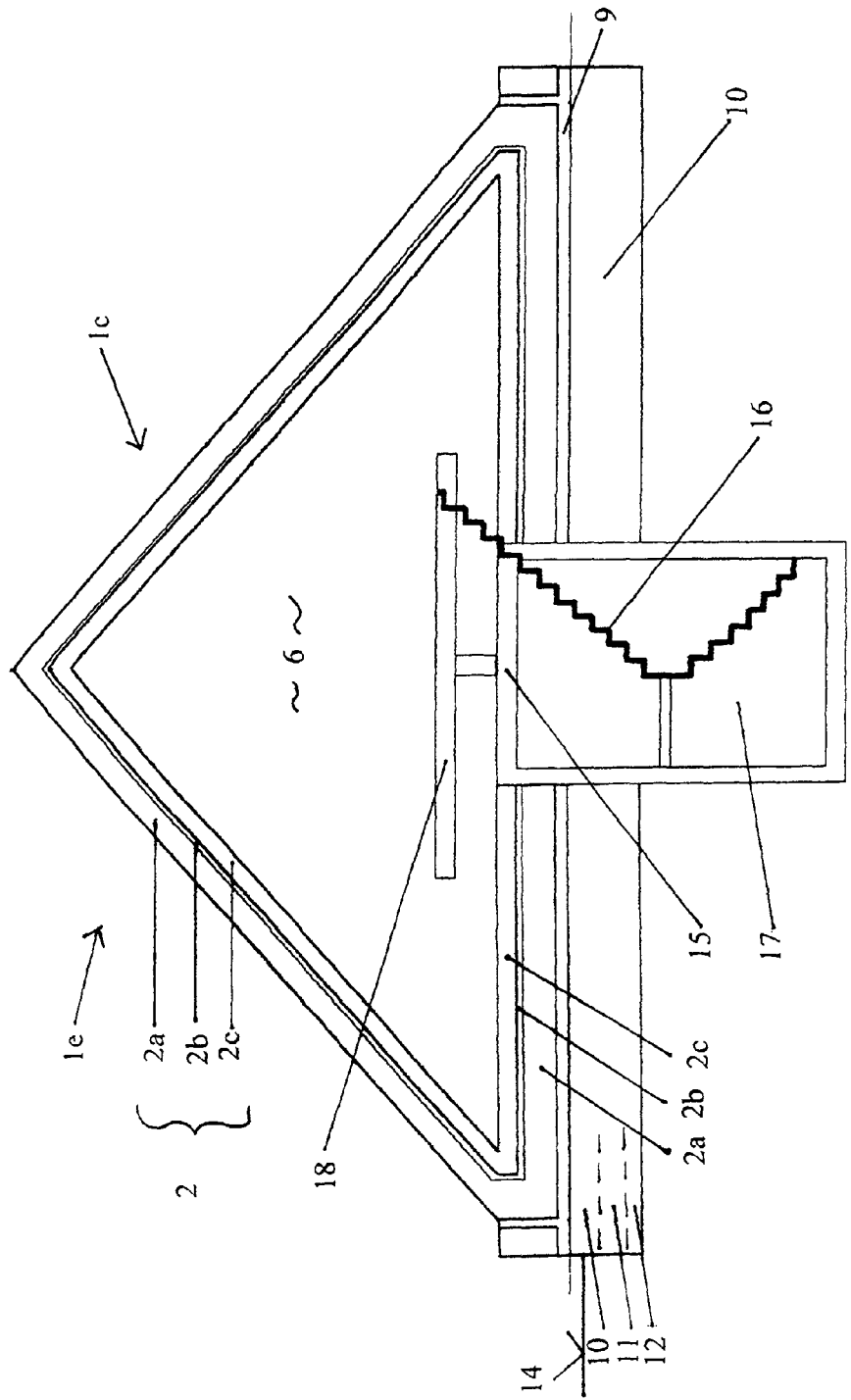
FIG. 4 shows the section of the pyramid building from the entrance, without the side wall 1b.

FIG. 4 shows the section drawing of the pyramid building from the entrance, without side wall 1b. The pyramid-shaped internal space 6 with the podium 18 and the internal entrance 15 implemented on the base is clearly shown on the section drawing. The internal entrance 15 is implemented on the base, as openings or windows may not be cut into the side walls because such an opening would interfere with the emergence of pyramid energy in the internal space 6. The object or person to be energized is usually placed on the podium 18, the most advantageous height of which is one-third of the height m, shown in FIG. 2, of the pyramid building 1, but the podium 18 in FIG. 4 may be also made to be of adjustable height. The internal entrance 15 and from there the podium 18 may be approached by stairs 16 through a tunnel 17 below the base which tunnel 17 may lead to the external entrance. See also FIG. 5 for a side view showing the tunnel 17 and the external entrance 19. In FIG. 4, only the external layer 2a, the middle layer 2b, and the internal layer 2c are indicated, but their construction units—such as the walling units or the covering units—are not. The foundation placed into the ground is also shown as a unit and its individual layers—such as the sand layer 12, the crushed rock-bed 11, and the steel-concrete 10—are indicated with dotted lines at the lower left corner. The steel-concrete 10 emerges from the ground, and the ground level 14 is also indicated at the edges. The entire pyramid building is built on the base insulator plate 9—which seals water and electricity from the foundation—placed on the steel-concrete 10.

Figure 5:
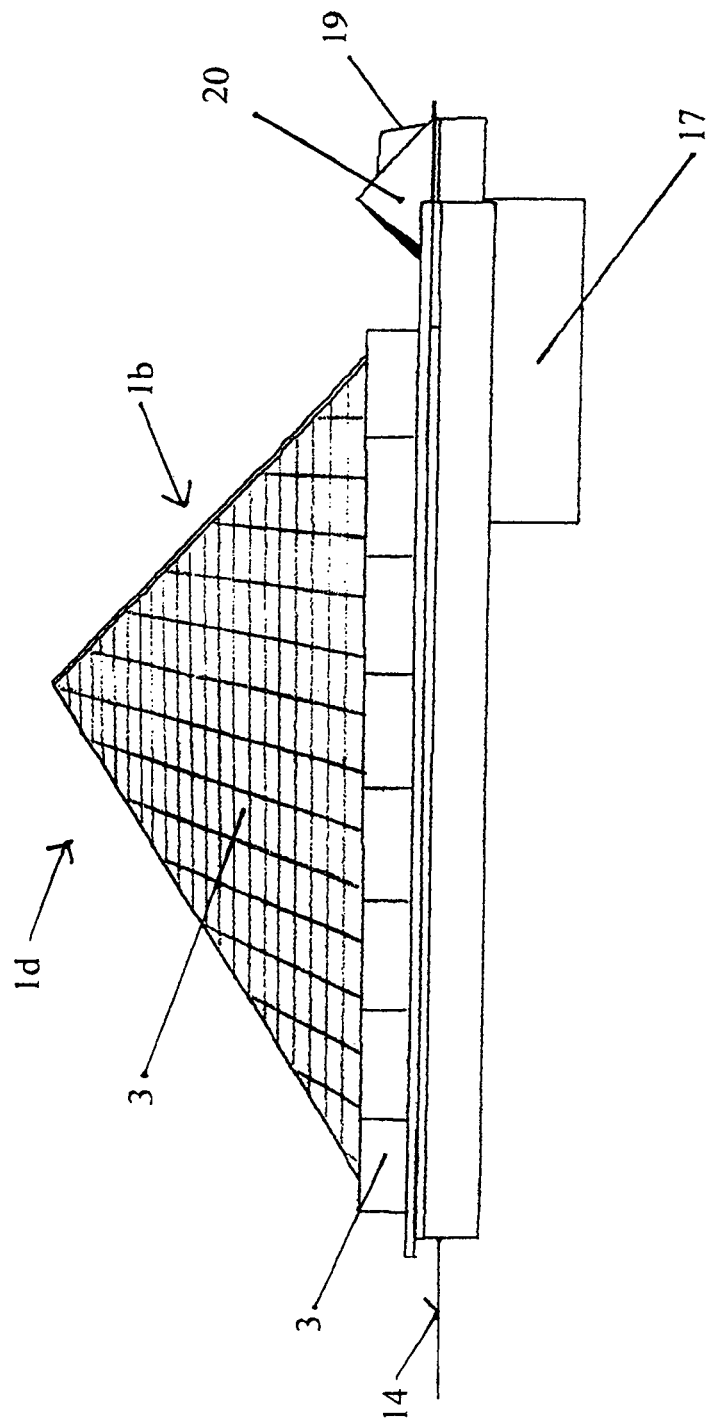
FIG. 5 shows the schematic drawing of the pyramid building from the side wall 1e.

FIG. 5 shows the schematic drawing of the pyramid building from the side wall, with the pyramid-shaped entrance building 20 and with the external entrance 19 thereon, as well as with the tunnel 17. The walling units 3—made of limestone bricks—are visible on a side wall forming a part of the pyramid building.

Figure 6:
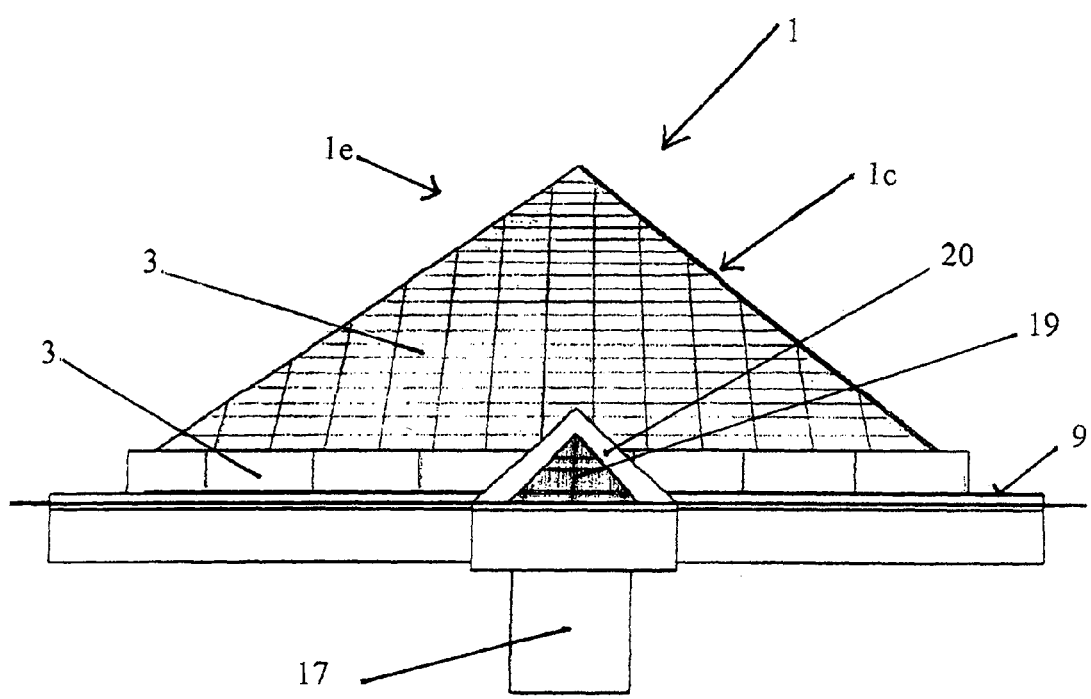
FIG. 6 shows the schematic drawing of the pyramid building from the entrance 19 and from the side wall 1b.

FIG. 6 shows the schematic drawing of the pyramid building 1 from the entrance 19. In this figure, the walling units 3 made of limestone bricks are shown on a side wall forming another part of the roof.

Figure 7:
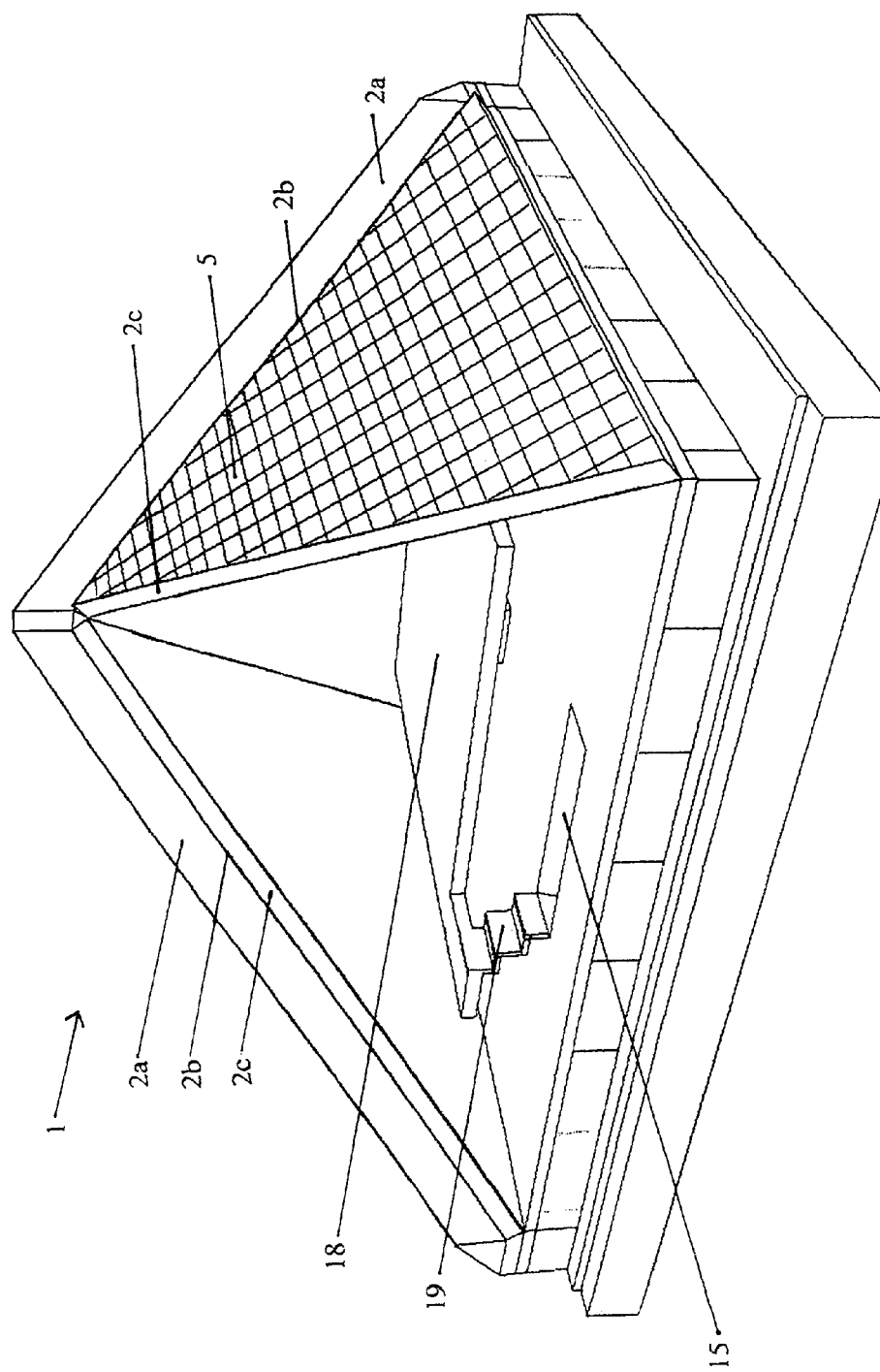
FIG. 7 shows the perspective view of the internal space of the pyramid building without side wall 1d and, in case of side wall 1e, without the external layer 2a and middle layer 2b.

FIG. 7 shows the perspective view of the internal space of the pyramid building 1 without a side wall and, in case of another side wall, without the external layer 2a and middle layer 2b. This way the transparent or translucent covering units 5 made of native salt become visible on a side wall, on which the piezoelectric units providing small amplitude vibration and the blue LEDs are fitted. However, these are not shown in FIG. 7. Their fitting on the covering unit 5 is shown on FIGS. 8 and 9. The presentation of the external layer 2a, the middle layer 2b, and the internal layer 2c is appropriately identical to that presented in FIG. 4. FIG. 7 also clearly shows—from another angle—the opening for the internal entrance 15 on the base and the upper part of the stairs leading to the podium 18.

Figure 8:
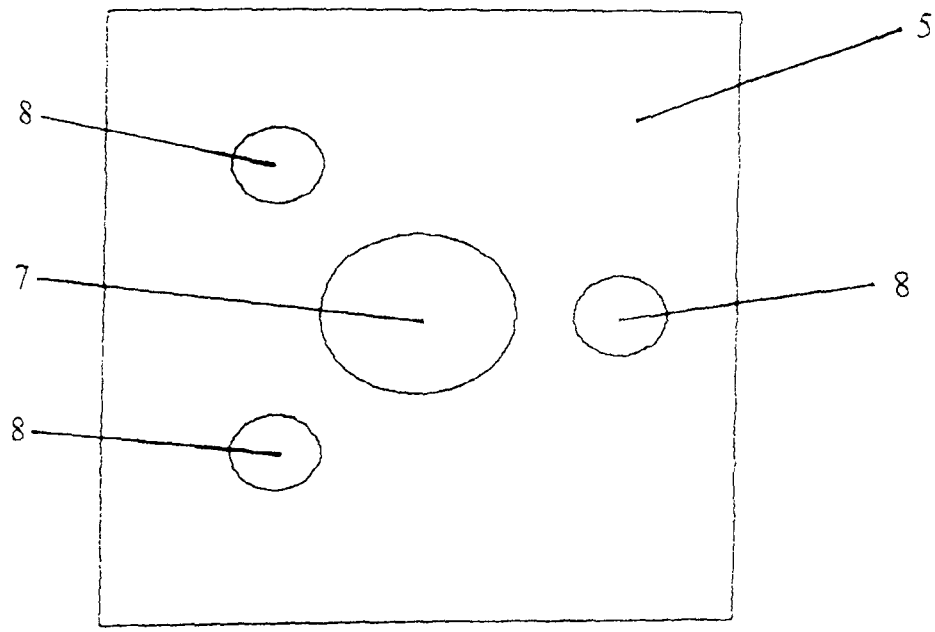
FIG. 8 shows the bird's-eye view of a covering unit 5 fitted in the middle with a piezoelectric unit 7 surrounded by three blue LEDs 8.

FIG. 8 shows the bird's-eye view of a covering unit 5 fitted in the middle with a piezoelectric unit 7 providing small amplitude vibration and with the three polarized blue LEDs 8 around it. In our description, LED stands for the English abbreviation of light emission diodes, which is a common expression for photodiodes. According to our invention, the LEDs 8 are to be fitted so that as much of their light as possible enters the internal space 6 of the pyramid building 1 through the transparent or translucent covering unit 5. In one advantageous embodiment according to the invention, the covering units 5 are cut from mined native salt panels.

Figure 9:
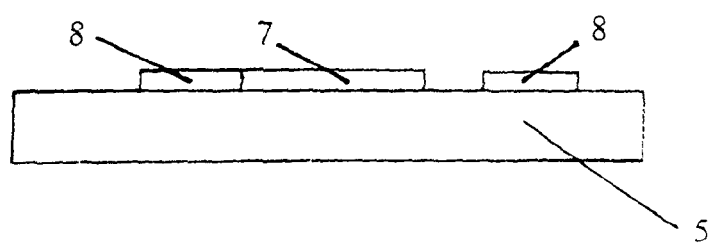
FIG. 9 shows the side view of the covering unit 5—as shown on FIG. 8—with the fitted piezoelectric unit 7 and the LEDs 8.

FIG. 9 shows the side view of the covering unit 5 shown in FIG. 8. Our invention is not limited to the embodiment shown in FIGS. 8 and 9, because one covering unit 5—in comparison to these Figures—may be fitted with even more piezoelectric units 7 and/or the LEDs 8 following other patterns as well. It is advantageous for the implementation of the pyramid building if piezoelectric unit 7 and/or LEDs 8 are fitted on some of the covering units 5—preferably more than 40% thereof—on parts of the side walls.

Figure 10:
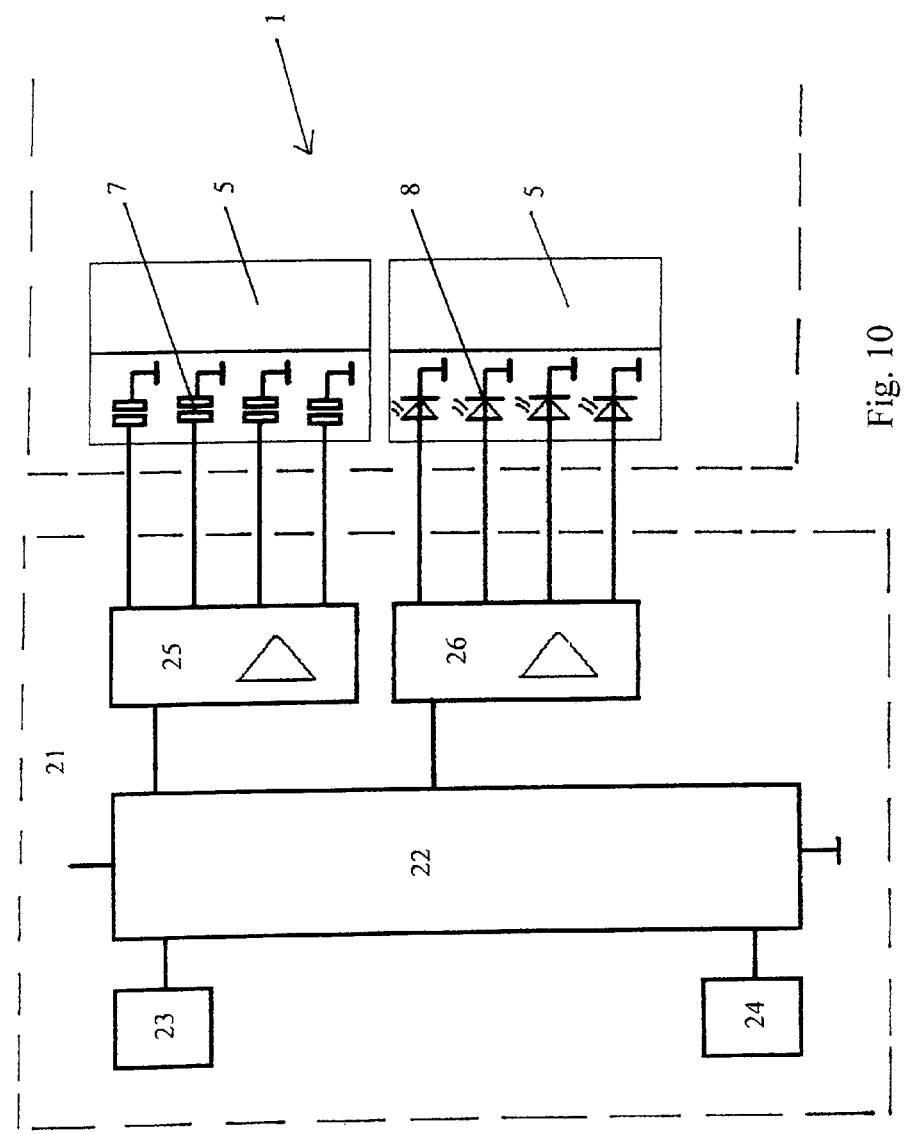
FIG. 10 shows the block schematic drawing of the control device 21 used to operate the pyramid building, with the connected piezoelectric bodies and LEDs already installed inside the pyramid building.

FIG. 10 shows the block schematic drawing of the control device 21 used to operate the pyramid building 1, with the connected piezoelectric units 7 and LEDs 8 already installed inside the pyramid building. The central control device 21 is equipped with at least one oscillator 23, at least one sensor unit 24 for detecting earth radiation and other surrounding radiations, with a control unit 22, with a driver unit 25, and with an operating unit 26. FIG. 10 does not show units that are necessary and commonly known for electric devices, such as power supplies, generators etc.

The pyramid building may be used without separate external control devices, as the pyramid energy generally emerges in pyramid buildings of appropriate size and proportions with isosceles triangle-shaped side walls and square bases. See Egyptian pyramids. The multi-layered walls according to our invention are suitable replacements for the thick walls of pyramids. However, emergence of the pyramid energy may be enhanced and controlled by turning on and operating the piezoelectric units 7 and LEDs 8 built into the side walls of the pyramid building 1. Thus, the central control device 21 is electrically connected with cables to the piezoelectric units 7 providing small amplitude vibration and to the blue LEDs 8 fitted onto the covering units 5 in the side walls of the internal space of the pyramid-shaped building 1. After the connection is established, the piezoelectric units 7 and LEDs 8 are turned on sequentially, first on one side wall, then on the subsequent side wall, then on the third side wall, then on the fourth side wall. The sequential vibration and lighting of the side walls continues in a clockwise direction. It is also possible to change the energizing effect, as the process may be initiated and carried on in a counter-clockwise direction as well. In such cases, the piezoelectric units 7 and the LEDs 8 are initiated by activating, as shown in FIG. 3, side wall 1b first, followed by side wall 1c, side wall 1d, and lastly, by side wall 1e.

The continuous circular activation procedure may be initiated, interrupted, or re-initiated at any side wall. It is also advantageous, as shown in FIG. 10, if the control unit 22 of the central control device 21 is synchronized with the Schumann frequency measured by the sensor unit 24 or selected by the operator, and if the faster or slower speed of the circular activation procedure is adjusted in the meantime, depending on whether the energy level of the object or person to be energized is to be increased or reduced, thereby providing a stress reducing effect.

As described above in relation to the state of the art, the utilization of pyramid energy has been an exciting issue for mankind since the ancient ages, and still several Hungarian and foreign inventions are created for this purpose. See the energy collector sunhat, the growth accelerating device, etc.

The advantages of the pyramid building according to our invention may be summarised as follows: in the pyramid-shaped space left in the pyramid building implemented according to our invention using multi-layered walls we can ensure advantageous circumstances that had been created so far only inside pyramids with several meters thick walls. In addition, the internal space is surrounded by electrically controllable, preferably amorphous, native salt panels dominated by negative ions. These have a twofold effect. On the one hand, the negative ions discharged by the salt have beneficial effects for various diseases—for further details see the salt therapeutic effects of salt caves. On the other hand, one of the major advantages of our invention is that, using the piezoelectric bodies built into and vibrating the covering units and the LEDs emitting polarized blue light, as well as the central device operating them, we can change the pyramid energy emerging or created in the internal space, according to our intention to increase or reduce the energy level of or relax the object or person to be energized. The pyramid building and the procedure for the operation thereof according to our invention is thus especially suitable for restoring the bio-vibration of the human body to ensure that the cells enjoy the most suitable vibration energy in the appropriate frequency range; they are well balanced, and are elevated to a higher vibration level, thus strengthening the electro-magnetic energy shell and aura of the human body. The pyramid building may also be an important and highly profitable accessory for health hotels, spas, health care centres, and tourist locations providing a wellness weekend and specialized services. It may also be used as a meditation centre providing mental and physical regeneration.

The invention claimed is:

1. A quadrilateral pyramid-shaped building, comprising:
   isosceles triangle-shaped supporting side walls;
   a square-shaped base;
   a pyramid-shaped internal space;
   a podium arranged in the pyramid-shaped internal space;
   wherein the side walls and the base are made of plural layers including an internal layer, an external layer, and a middle layer;
   electrically controllable covering units configured to form the internal layer of the side walls and the internal layer of the base;
   a water and electric insulating plate arranged beneath the side walls; and
   piezoelectric units fitted onto outer sides of the covering units forming the internal layer of the side walls and the internal layer of the base and arranged to face the pyramid-shaped internal space;
   wherein the middle layer is configured to fasten the internal layer and the external layer together.

2. The pyramid-shaped building according to claim 1, further comprising:
   LEDs configured to emit polarized blue light into the pyramid-shaped internal space and arranged onto the outer sides of the covering units around the piezoelectric units;
   wherein the covering units are transparent or translucent.

3. The pyramid-shaped building according to claim 1, further comprising:
   layers of sand, crushed rock-bed, and steel-concrete laid in that order under the water and electric insulating plate with the steel-concrete next to the insulating plate.

4. The pyramid-shaped building according to claim 1, further comprising:
   an internal entrance configured to allow entry through the base into the pyramid-shaped internal space;
   stairs configured to lead from below the base up to the internal entrance;
   a tunnel formed below the layers of sand, crushed rock-bed, and steel-concrete, and configured to permit access to the stairs;
   a pyramid-shaped entrance building being constructed outside the pyramid-shaped building and leading to the tunnel; and
   an external entrance located in front of the pyramid-shaped entrance building.

5. The pyramid-shaped building according to claim 1, wherein at least part of the pyramid-shaped building is limestone bricks.

6. The pyramid-shaped building according to claim 1, wherein each of the piezoelectric units is formed substantially circular in shape, fitted into a center of each of the outer sides of the covering units, and surrounded by at least three of the LEDs configured to emit polarized blue light.

7. The pyramid-shaped building according to claim 1, further comprising:
   a central control device including an oscillator, a sensor unit configured to detect earth radiation, a control unit, a driver unit for the piezoelectric units, and an operating unit for the LEDs.

8. A procedure for operation of the pyramid-shaped building according to claim 7, wherein the central control device is electrically connected to the piezoelectric units by the driver unit and to the LEDs by the operating unit, and
   after the central control device is electrically connected, the piezoelectric units and the LEDs are turned on, at first on one of the side walls, then on another of the side walls, then on a third of the side walls, then on a fourth of the side walls, then sequential lighting of the side walls is continued in a clockwise or a counter-clockwise direction;
   wherein the procedure is initiated, interrupted, or re-initiated at any of the side walls while the control unit of the central control device is synchronized at a frequency measured by the sensor unit or selected by the operator; and
   wherein a speed of the procedure is adjusted faster or slower during the operation of the pyramid-shaped building.

* * * * *